United States Patent
Shih

(12) 
(10) Patent No.: US 7,646,000 B2
(45) Date of Patent: Jan. 12, 2010

(54) PORTABLE STERILIZER

(76) Inventor: Men-Tzon Shih, No.14-2, Lane 2, Shanjiao Rd., 11 Neighborhood, Dahua Village, Niaosong Township, Kaohsiung County 833 (TW)

( * ) Notice: Subject to any disclaimer, the term of this patent is extended or adjusted under 35 U.S.C. 154(b) by 495 days.

(21) Appl. No.: 11/448,111

(22) Filed: Jun. 7, 2006

(65) Prior Publication Data

US 2008/0067419 A1    Mar. 20, 2008

(51) Int. Cl.
*A61L 3/00*    (2006.01)
(52) U.S. Cl. ................... 250/455.11; 422/24
(58) Field of Classification Search ............ 250/455.11; 422/24
See application file for complete search history.

(56) References Cited

U.S. PATENT DOCUMENTS 5,029,252 A * 7/1991 Ameseder .............. 250/455.11
5,487,877 A * 1/1996 Choi ......................... 422/300
6,461,568 B1 * 10/2002 Eckhardt .................... 422/24
6,953,940 B2 * 10/2005 Leighley et al. ......... 250/455.11

* cited by examiner

*Primary Examiner*—Kiet T Nguyen
(74) *Attorney, Agent, or Firm*—Muncy, Geissler, Olds & Lowe, PLLC

(57) ABSTRACT

A portable sterilizer is disclosed. The portable sterilizer is composed of a housing for carrying and a sterilization device such as a UV light or an ozone generator inside the housing. A chamber with certain space is disposed inside the housing, connecting with the sterilization device for being disinfected. An opening is on the housing for putting tableware such as knives, forks, spoons or chopsticks inside the chamber to be sterilized by UV light or ozone gas. Thus users can carry the present invention with them and sterilize tableware or daily essentials easily.

10 Claims, 4 Drawing Sheets

PORTABLE STERILIZER

BACKGROUND OF THE INVENTION

The present invention relates to a portable sterilizer, especially to an independent sterilizer that users can carry with them and convenient for use for providing sterilized tableware such as forks, knives, spoons and chopsticks. The tableware can be fully and partly mounted inside the sterilizer for disinfection.

Conventional ways uses UV light or ozone gas for disinfection, sterilization, or air purification purposes. Such kind of technology has been applied to medical devices or articles for daily use such as disinfection of telephone receivers, computer mouse, or water faucets. The area we often contact is the most bacteria-infested positions. It is necessary to sterilize for reducing risk of bacteria spread and infection. Moreover, the ozone generator can get power from vehicles so as to purify air therein. The ozone or UV light sterilization will not generate bad smell such as chloride disinfection so that they are especially suitable for sterilization of tableware. Compared with conventional detergents, the sterilizing effect of UV light and ozone gas is far more better. Furthermore, some bacteria such as gram-negative bacteria may have resistance to detergent. UV light and ozone gas can kill such bacteria. However, conventional ultraviolet or ozone sterilization machines are fixed on some equipment such as dishwashers and are not portable. As to eating out people, there is a need to have some kind of portable sterilizer for cleaning and disinfection of the tableware used in some eateries or restaurants.

SUMMARY OF THE INVENTION

Therefore it is a primary object of the present invention to provide a portable sterilizer which includes a portable housing with a chamber and a sterilization device such as UV light or ozone generator, connecting with each other. An opening is mounted on the housing so that the whole or part of tableware can be disposed inside the chamber of the equipment for being sterilized by UV light or ozone. The present invention is portable and convenient for use.

It is another object of the present invention to provide a portable sterilizer that gets power from internal batteries or from external power source. Also a timer is disposed on the sterilizer for presetting operation time of the UV light or the ozone generator. Thus the equipment is able to be turned off automatically. This enhances the convenience of operation.

It is a further object of the present invention to provide a portable sterilizer that includes a housing made from transparent plastic or glass so that users can see elements therein and the operation condition. Moreover, user can sight whether a lamp of the UV light need to be changed or not. This improves the convenience of operation.

DETAILED DESCRIPTION OF THE PREFERRED EMBODIMENT

Figure 1:
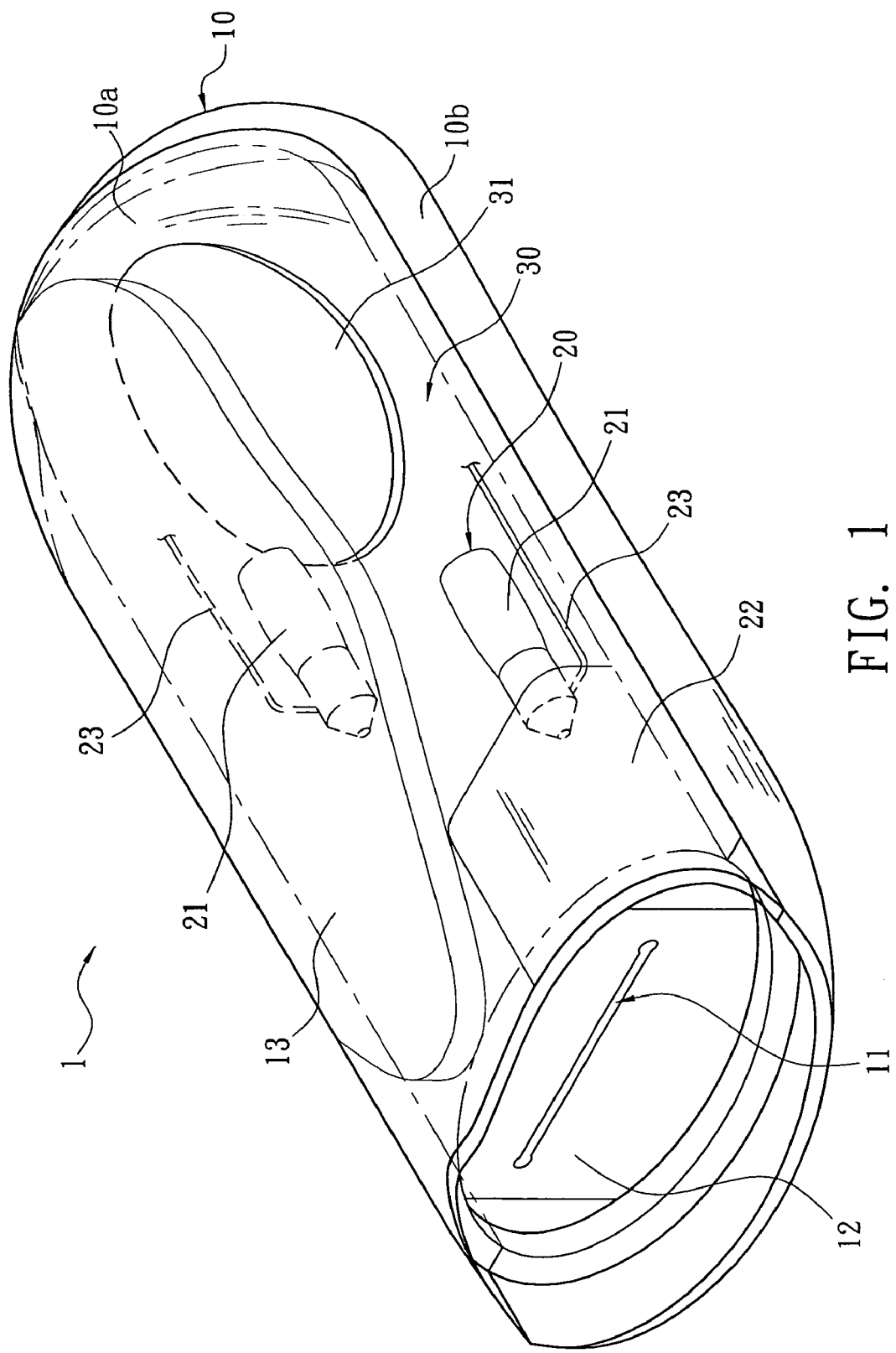
FIG. 1 is a perspective view of an embodiment in accordance with the present invention.

Refer from FIG. 1 to FIG. 4, a sterilizer 1 according to the present invention consists of a housing 10, a sterilization device 20 disposed inside the housing 10, and a chamber 30 inside the housing 10. The housing is compact and portable, easy to be put inside a bag or a packet of users. The sterilization device 20 can be UV light 21, as shown in figure or an ozone generator (not shown in figure). A battery holder 22 containing batteries is mounted inside the housing 10 or the sterilizer 1 can also connect with external power sources for supplying power. The chamber 30 is designed according to the style of the housing 10 and the sterilization device 20 with certain space connecting with the sterilization device 20 such as UV light 21 or ozone generator so as to make the chamber 30 be sterilized by the sterilization device 20.

An opening 11 connecting with the chamber 30 is mounted on the housing 10. Thus part 201 or whole of the tableware 2 such as knives, forks, spoons and chopsticks can be set inside the chamber 30 through the opening 11 to be exposed to UV light or ozone gas generated from the sterilization device 20 for sterilization and disinfection. After performing the sterilization process, the tableware 2 is taken out and used.

Figure 2:
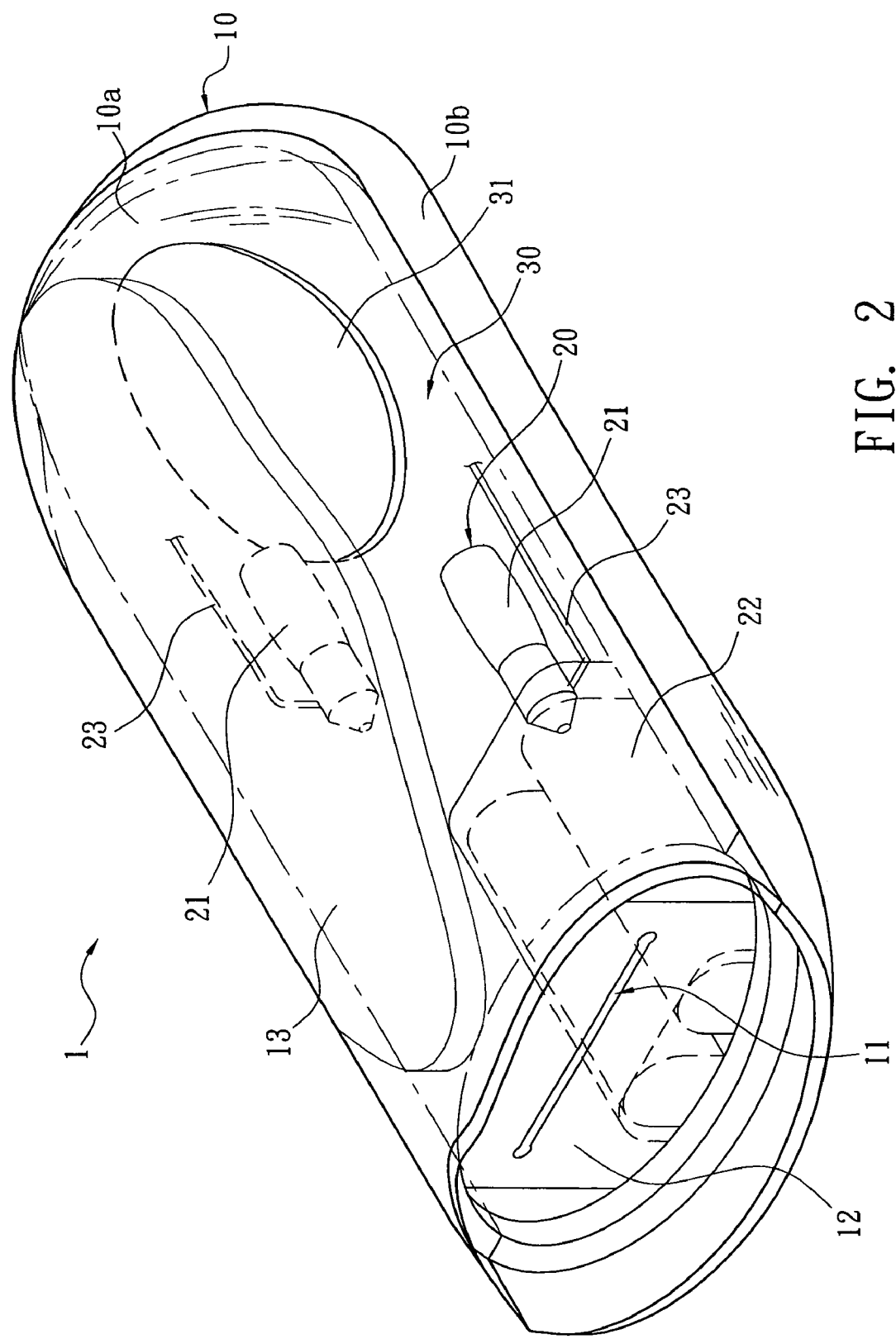
FIG. 2 is a perspective view of an embodiment in accordance with the present invention.
Figure 3:
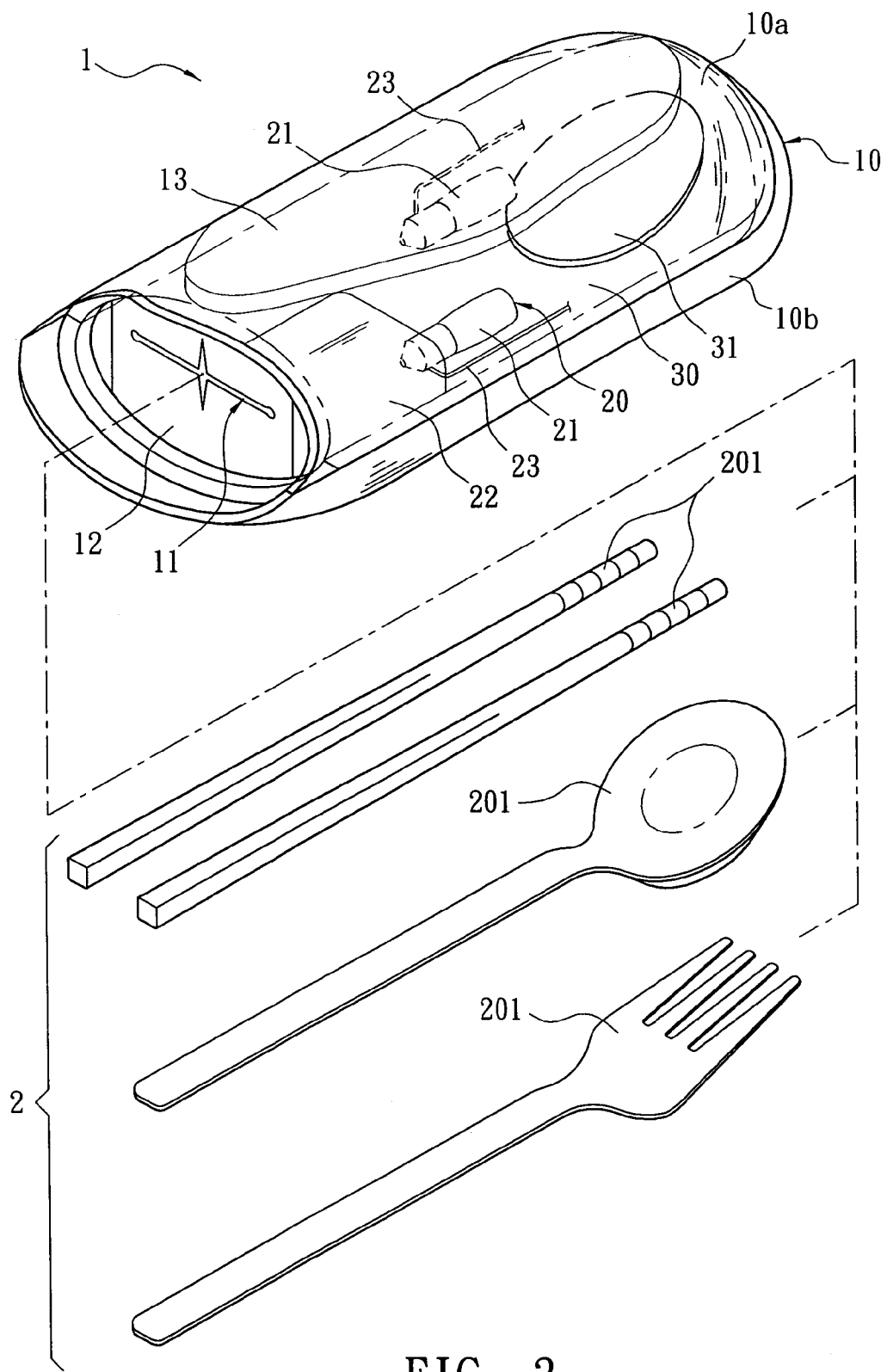
FIG. 3 is a status of an embodiment according to the present invention in combination with tableware before used.
Figure 4:
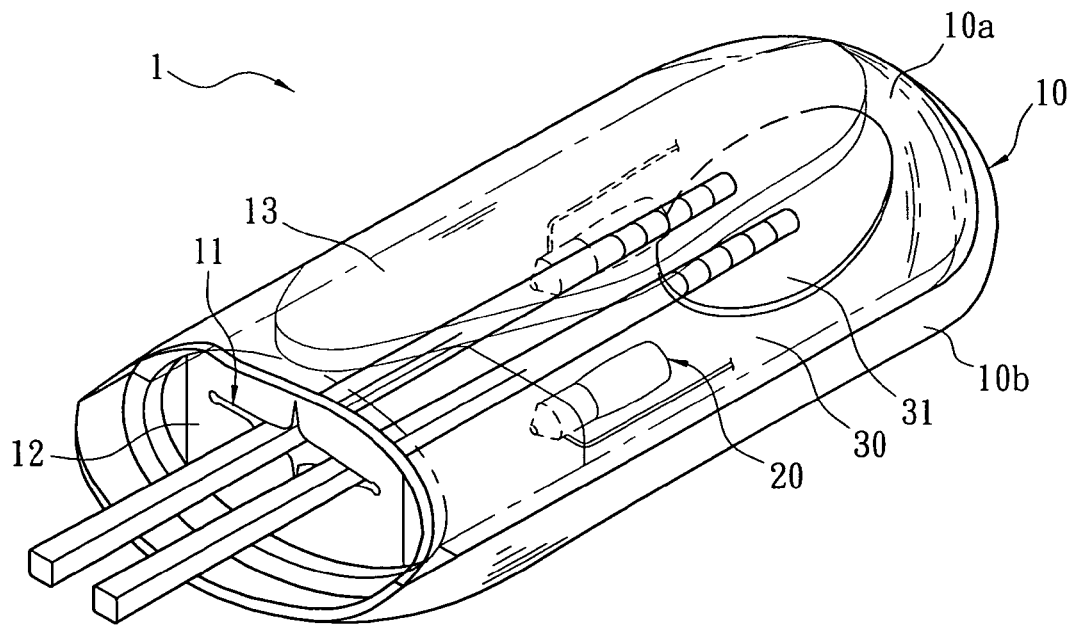
FIG. 4 is a status of an embodiment according to the present invention in combination with tableware after used.

There is no limitation on shape of the housing 10 of the sterilizer 1. It can be a cuboid formed by an upper half 10a and a lower half 10b so as to make the chamber 30 have certain length. The length of the housing or the chamber 30 is preferably shorter than the length of the tableware 2 such as knives, forks, spoons or chopsticks. And the opening 11 is preferably arranged on one end of the housing 10, as shown from FIG. 1 to FIG. 4. Thus the size of the sterilizer 1 is minimized and compact for the convenience of carrying while traveling or eating out. In usage, users only need to put part 201 of the tableware 2 such as knives, forks, spoons, or chopsticks inside the chamber 30 of the housing 10 through the opening 11, as shown in FIG. 3 & FIG. 4 to be sterilized for sanitary needs.

The housing is made by hard material that the UV light can't penetrate. For example, plastic or glass is suitable material. The material can also be transparent such as clear plastic or glass, as shown from FIG. 1 to FIG. 4. Thus users can look inside the housing. Or a transparent window (not shown in figure) is arranged on the opaque housing 10 so that uses can see internal parts of the sterilizer 1 anytime. Also they can check whether the light bulb of the UV light 21 on the sterilization device 20 needs to be changed or not. Thus the convenience of operation is improved. If the sterilization device 20 is the UV light 21, mirrors 13 or other material able to reflect or diffuse light are disposed on inner surface of the housing 10 so as to make the UV light emitted from the UV light 21 fill the space of the chamber 30 through reflection of diffuse reflection of the mirrors. Thus the tableware 2 inside the chamber 30 is fully and effectively disinfected. There is at least one UV light bulb 21. In the embodiment shown in figure, there are two UV light bulbs 21. Moreover, a connecting wire 23 between the two UV light bulbs 21 is properly arranged inside the housing, separating with the chamber 30 without influence on input or output of the objects to be sterilized.

The sterilized 1 according to the present invention further includes a timer so as to preset operating time of the sterilization device 20 and turn off the sterilization device 20 automatically. Furthermore, an indicator lamp or a control switch can be disposed on outer surface of the housing 10 so as to control or show on/off status of the sterilization device 20 inside for the convenience of users.

There is no limit on shape of the opening 11, depending on objects to be sterilized. For users, it should be easy and convenient to put the tableware 2 inside the chamber 30 through the opening 11. As shown in FIG. 1 & FIG. 2, the opening 11 can be an I-shaped slot, or a cross-shaped opening in FIG. 3. The opening 11 is preferably elastically sealed. Thus after setting the objects to be sterilized inside the chamber 3o through the opening 11, the opening 11 is elastically sealed automatically so as to prevent leakage of UV light or ozone gas. Furthermore, the elastic-sealed opening 11 is designed with various structure and material. For example, the material such as foam, rubber, silicon is used to form an elastic washer 12 with certain thickness and the elastic washer 12 is. fixed on the location of the opening 11 by mounting, glued, or threaded. Then a hole/slot is located on the elastic washer 12, as shown from FIG. 1 to FIG. 4. When the object to be sterilized is put into the chamber 30 through the opening 11, the opening 11 is enlarged by the object while the elastic washer 12 elastically attached on the object so as to seal the opening. Moreover, the object with part thereof extended outside the opening 11 is also clipped by elasticity of the opening 11 so as to prevent shaking or falling off. Moreover, a bearing 31 is arranged on an end of the chamber 30 opposite to the end with the opening 11 so that the object inside the chamber 30 can lean against the bearing 31.

Figure 5:
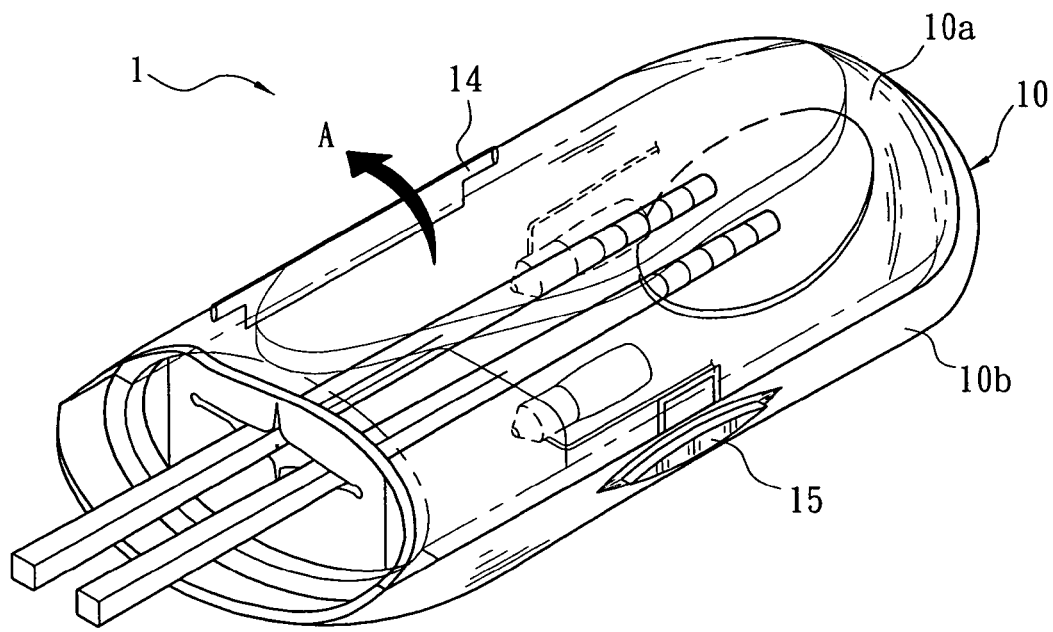
FIG. 5 is a perspective view of another embodiment in accordance with the present invention.

In addition, besides the opening 11 disposed on one end of the cuboid housing 10, the opening 11 can be designed with a lifted cover, as embodiment in FIG. 5 for sterilization of small objects such as pacifiers, pipes, or mail clippers. The housing 10 consists of the upper half 10a and the lower half 10b. A pivot 14 is disposed on one lateral side of the housing 10 while a locking member 15 is set on the other side. In usage, the locking member 15 is pressed for being out of the locking status. The upper half 10a is pivoted upwards (as shown in arrow A) so that the while object to be sterilized can be put into the chamber 30. Then lock the upper half 10a to form a close space for sterilization. After sterilization process, lift up the upper half 10a and take out the object. As to the sterilization device 20 including the UV light 21, ozone generator, or connecting wires 23, it is connected with the end with the pivot 14. Thus no matter it's on the upper half 10a or the lower half 10b, there is no influence on the electrically connection or the operation.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A portable sterilizer comprising a housing, a sterilization device, and a chamber, wherein the housing is a portable housing;
    the sterilization device disposed inside the housing and driven by power from a power source for disinfecting objects;
    the chamber arranged inside the housing, connecting with the sterilization device so as to have sterilization effect; the chamber connecting with outside by an opening on the housing, wherein the opening is an I-shaped or cross-shaped slot locating on a washer made from soft elastic material in order to elastically seal the opening;
    the whole or part of the objects to be sterilized are put into the chamber through the opening and then the sterilization device is turned on to disinfect whole or part of the objects.

2. The portable sterilizer as claimed in claim 1, wherein the sterilization device is a UV light.

3. The portable sterilizer as claimed in claim 2, wherein mirrors or other material able to reflect or diffuse light are disposed on inner surface of the housing.

4. The portable sterilizer as claimed in claim 2, wherein there is at least one UV light.

5. The portable sterilizer as claimed in claim 1, wherein the sterilization device is an ozone generator.

6. The portable sterilizer as claimed in claim 1, wherein the power source is battery inside a battery holder on the housing or an external power source.

7. The portable sterilizer as claimed in claim 1, wherein the housing is made from transparent material for seeing inside.

8. The portable sterilizer as claimed in claim 1, wherein a control switch or an indicator light is arranged on outer surface of the housing.

9. The portable sterilizer as claimed in claim 1, wherein a bearing is disposed on an end of the chamber opposite to the end with the opening so that the object to be sterilized leans against the bearing.

10. The portable sterilizer as claimed in claim 1, wherein the housing having an upper half and a lower half, connecting with each other by a pivot so as to make the upper half is lift upwards.

* * * * *